(12) United States Patent
Neyer

(10) Patent No.: US 8,218,711 B2
(45) Date of Patent: Jul. 10, 2012

(54) REPLACEABLE ACCESSORY FOR A SMALL ELECTRICAL APPLIANCE AND METHOD OF MONITORING THE USAGE OF THE ACCESSORY

(75) Inventor: Christian Neyer, Eschborn (DE)

(73) Assignee: Braun GmbH, Kronberg (DE)

( * ) Notice: Subject to any disclaimer, the term of this patent is extended or adjusted under 35 U.S.C. 154(b) by 1213 days.

(21) Appl. No.: 11/722,675

(22) PCT Filed: Dec. 16, 2005

(86) PCT No.: PCT/EP2005/013559
§ 371 (c)(1),
(2), (4) Date: Jun. 22, 2007

(87) PCT Pub. No.: WO2006/069644
PCT Pub. Date: Jul. 6, 2006

(65) Prior Publication Data
US 2011/0122987 A1   May 26, 2011

(30) Foreign Application Priority Data

Dec. 23, 2004   (DE) .......................... 10 2004 062 150

(51) Int. Cl.
*G07C 3/00* (2006.01)
(52) U.S. Cl. ........................................... 377/15; 377/16
(58) Field of Classification Search .................... 377/15, 377/16
See application file for complete search history.

(56) References Cited

U.S. PATENT DOCUMENTS

| 2,798,241 | A | 7/1957 | Cohen |
| 3,109,619 | A | 11/1963 | Krug et al. |
| 3,220,039 | A | 11/1965 | Dayton et al. |
| 3,417,417 | A | 12/1968 | Rhodes |
| 3,461,874 | A | 8/1969 | Martinez |
| 3,496,500 | A | 2/1970 | Romary |
| 3,571,544 | A | 3/1971 | Sheehan |
| 3,782,799 | A | 1/1974 | Hansen |
| 3,796,850 | A | 3/1974 | Moreland, II et al. |
| 3,802,420 | A | 4/1974 | Moffat et al. |
| 3,810,147 | A | 5/1974 | Lichtblau |
| 3,904,841 | A | 9/1975 | Swatman |
| 4,156,620 | A | 5/1979 | Clemens |

(Continued)

FOREIGN PATENT DOCUMENTS

CN         2048697         12/1989

(Continued)

OTHER PUBLICATIONS

Office Action from U.S. Appl. No. 10/872,075, dated Mar. 24, 2006.

(Continued)

*Primary Examiner* — Lincoln Donovan
*Assistant Examiner* — William Hernandez
(74) *Attorney, Agent, or Firm* — John P. Colbert

(57) ABSTRACT

An accessory for a small electrical appliance, such as a brush attachment for an electric toothbrush or a shaving component for an electric shaving apparatus, including a data memory and a transponder. The accessory includes an electronic circuit that modifies a value stored in the data memory each time the electronic circuit receives a corresponding signal. Also described is a method of determining the end of the period of use of the accessory.

13 Claims, 2 Drawing Sheets

U.S. PATENT DOCUMENTS

| | | | |
|---|---|---|---|
| 4,274,070 A | 6/1981 | Thiene |
| 4,333,197 A | 6/1982 | Kuris |
| 4,349,814 A | 9/1982 | Akehurst |
| 4,352,098 A | 9/1982 | Stephen et al. |
| 4,365,376 A | 12/1982 | Oda et al. |
| 4,371,118 A | 2/1983 | Sontheimer et al. |
| 4,413,199 A | 11/1983 | Fischer |
| 4,492,574 A | 1/1985 | Warrin et al. |
| 4,502,497 A | 3/1985 | Siahou |
| 4,506,400 A | 3/1985 | Klein |
| 4,514,172 A | 4/1985 | Behringer |
| 4,523,083 A | 6/1985 | Hamilton |
| 4,546,266 A | 10/1985 | Zenick et al. |
| 4,553,252 A * | 11/1985 | Egendorf ........................ 377/15 |
| 4,595,850 A | 6/1986 | Woog |
| 4,682,584 A | 7/1987 | Pose |
| 4,698,869 A | 10/1987 | Mierau et al. |
| 4,704,602 A | 11/1987 | Asbrink |
| 4,716,614 A | 1/1988 | Jones et al. |
| 4,736,207 A | 4/1988 | Siikaria et al. |
| 4,820,152 A | 4/1989 | Warrin et al. |
| 4,827,550 A | 5/1989 | Graham et al. |
| 4,845,796 A | 7/1989 | Mosley |
| 4,878,679 A | 11/1989 | Plank et al. |
| 4,900,252 A | 2/1990 | Liefke et al. |
| 4,910,634 A | 3/1990 | Pipkorn |
| 4,914,376 A | 4/1990 | Meyer |
| 5,014,794 A | 5/1991 | Hansson |
| 5,065,137 A | 11/1991 | Herman |
| 5,072,164 A | 12/1991 | Prius et al. |
| 5,099,536 A | 3/1992 | Hirabayashi |
| 5,165,131 A | 11/1992 | Staar |
| 5,184,959 A | 2/1993 | Oryhon et al. |
| 5,189,751 A | 3/1993 | Giuliani |
| 5,217,478 A | 6/1993 | Rexroth |
| 5,233,323 A | 8/1993 | Burkett et al. |
| 5,263,218 A | 11/1993 | Giuliani et al. |
| 5,269,794 A | 12/1993 | Rexroth |
| 5,289,604 A | 3/1994 | Kressner |
| 5,305,492 A | 4/1994 | Giuliani et al. |
| 5,337,435 A | 8/1994 | Krasner et al. |
| 5,341,534 A | 8/1994 | Serbinski et al. |
| 5,355,544 A | 10/1994 | Dirksing |
| 5,378,153 A | 1/1995 | Giuliani et al. |
| 5,381,576 A | 1/1995 | Hwang |
| 5,392,028 A | 2/1995 | Pichl |
| 5,438,726 A * | 8/1995 | Leite ................................ 15/105 |
| 5,502,861 A | 4/1996 | Spieler et al. |
| 5,544,382 A | 8/1996 | Giuliani et al. |
| 5,561,881 A * | 10/1996 | Klinger et al. .................. 15/22.1 |
| 5,576,693 A | 11/1996 | Tyren et al. |
| 5,577,285 A | 11/1996 | Drossler |
| 5,581,469 A * | 12/1996 | Kim ................................ 702/34 |
| 5,673,451 A | 10/1997 | Moore et al. |
| 5,693,042 A | 12/1997 | Boiarski et al. |
| 5,749,885 A | 5/1998 | Sjostrom et al. |
| 5,760,580 A | 6/1998 | Tyren |
| 5,781,955 A | 7/1998 | Hendricks |
| 5,784,742 A | 7/1998 | Giuliani et al. |
| 5,812,065 A | 9/1998 | Schrott et al. |
| 5,815,872 A | 10/1998 | Meginniss, III et al. |
| 5,864,288 A | 1/1999 | Hogan |
| 5,888,031 A | 3/1999 | Buck et al. |
| 5,897,315 A | 4/1999 | Nakayama et al. |
| 5,930,858 A | 8/1999 | Jung |
| 5,939,983 A | 8/1999 | Rudell et al. |
| 5,943,723 A | 8/1999 | Hilfinger et al. |
| 5,974,615 A | 11/1999 | Schwarz-Hartmann et al. |
| 5,998,965 A | 12/1999 | Carlucci et al. |
| 6,017,354 A | 1/2000 | Culp et al. |
| 6,029,303 A * | 2/2000 | Dewan ............................ 15/105 |
| 6,031,762 A * | 2/2000 | Saitoh ...................... 365/185.24 |
| 6,043,646 A | 3/2000 | Jansseune |
| 6,081,957 A | 7/2000 | Webb |
| 6,140,723 A | 10/2000 | Matsui et al. |
| 6,163,258 A | 12/2000 | Rudell et al. |
| 6,177,870 B1 | 1/2001 | Lian et al. |
| 6,193,510 B1 | 2/2001 | Tsimerman |
| 6,195,828 B1 | 3/2001 | Fritsch |
| 6,202,242 B1 | 3/2001 | Salmon et al. |
| 6,212,052 B1 | 4/2001 | Heuer et al. |
| 6,227,853 B1 | 5/2001 | Hansen et al. |
| 6,234,051 B1 | 5/2001 | Bareggi |
| 6,265,789 B1 | 7/2001 | Honda et al. |
| 6,326,884 B1 | 12/2001 | Wohlrabe |
| 6,353,956 B1 | 3/2002 | Berge |
| 6,359,559 B1 | 3/2002 | Rudell et al. |
| 6,367,108 B1 | 4/2002 | Fritsch et al. |
| 6,389,633 B1 | 5/2002 | Rosen |
| 6,422,566 B1 | 7/2002 | Rudell et al. |
| 6,453,497 B1 | 9/2002 | Chiang et al. |
| 6,531,873 B1 | 3/2003 | Wohlrabe |
| 6,536,068 B1 | 3/2003 | Yang et al. |
| 6,545,576 B1 | 4/2003 | Marchini et al. |
| 6,590,763 B2 | 7/2003 | Kishimoto |
| 6,611,780 B2 | 8/2003 | Lundell et al. |
| 6,623,698 B2 | 9/2003 | Keo |
| 6,636,135 B1 | 10/2003 | Vetter |
| 6,648,641 B1 | 11/2003 | Viltro et al. |
| 6,731,213 B1 | 5/2004 | Smith |
| 6,734,795 B2 | 5/2004 | Price |
| 6,735,802 B1 | 5/2004 | Lundell et al. |
| 6,750,747 B2 | 6/2004 | Mandell et al. |
| 6,754,928 B1 | 6/2004 | Rosen |
| 6,792,640 B2 | 9/2004 | Levy et al. |
| 6,798,169 B2 * | 9/2004 | Stratmann et al. ............. 320/114 |
| 6,850,167 B2 | 2/2005 | Rosen |
| 6,868,919 B1 | 3/2005 | Manschitz et al. |
| 6,952,855 B2 | 10/2005 | Lev et al. |
| 6,954,961 B2 | 10/2005 | Ferber et al. |
| 7,024,717 B2 | 4/2006 | Hilscher et al. |
| 7,067,945 B2 | 6/2006 | Grez et al. |
| 7,086,111 B2 | 8/2006 | Hilscher et al. |
| 7,174,972 B2 | 2/2007 | Kristen et al. |
| 7,207,080 B2 * | 4/2007 | Hilscher et al. ................. 15/22.1 |
| 7,248,892 B2 | 7/2007 | White et al. |
| 7,258,546 B2 | 8/2007 | Beier et al. |
| 7,313,422 B2 | 12/2007 | White et al. |
| 7,373,170 B2 | 5/2008 | White et al. |
| 7,376,439 B2 | 5/2008 | White et al. |
| 7,411,511 B2 * | 8/2008 | Kennish et al. ............. 340/573.1 |
| 7,621,015 B2 | 11/2009 | Hilscher et al. |
| 7,624,467 B2 | 12/2009 | Hilscher et al. |
| 7,661,172 B2 * | 2/2010 | Hilscher et al. ................. 15/22.1 |
| 7,673,360 B2 * | 3/2010 | Hilscher et al. ................. 15/22.1 |
| 7,682,153 B2 * | 3/2010 | Hilfinger et al. ............... 433/216 |
| 7,770,251 B2 | 8/2010 | Hilscher et al. |
| 7,774,886 B2 | 8/2010 | Hilscher et al. |
| 7,784,144 B2 | 8/2010 | Renault |
| 7,861,349 B2 | 1/2011 | Hilscher et al. |
| 2002/0088068 A1 | 7/2002 | Levy et al. |
| 2002/0129454 A1 | 9/2002 | Hilscher et al. |
| 2002/0133308 A1 | 9/2002 | Lundell et al. |
| 2002/0196113 A1 | 12/2002 | Rudd et al. |
| 2003/0017874 A1 | 1/2003 | Jianfei et al. |
| 2003/0085687 A1 | 5/2003 | Stratmann et al. |
| 2003/0093103 A1 | 5/2003 | Malackowski et al. |
| 2003/0101526 A1 * | 6/2003 | Hilscher et al. ................. 15/22.1 |
| 2003/0115694 A1 | 6/2003 | Pace |
| 2003/0131427 A1 | 7/2003 | Hilscher et al. |
| 2003/0165794 A1 | 9/2003 | Matoba |
| 2004/0134000 A1 * | 7/2004 | Hilfinger et al. ................ 15/22.1 |
| 2004/0220602 A1 | 11/2004 | Deng et al. |
| 2004/0255409 A1 | 12/2004 | Hilscher et al. |
| 2004/0267297 A1 | 12/2004 | Malackowski |
| 2005/0000044 A1 | 1/2005 | Hilscher et al. |
| 2005/0011025 A1 | 1/2005 | Hilscher et al. |
| 2005/0050658 A1 | 3/2005 | Chan et al. |
| 2005/0128051 A1 | 6/2005 | Dickinson et al. |
| 2005/0269403 A1 | 12/2005 | White et al. |
| 2005/0271531 A1 | 12/2005 | Brown, Jr. et al. |
| 2005/0272001 A1 | 12/2005 | Blain et al. |
| 2005/0272002 A1 | 12/2005 | Chenvainu et al. |
| 2006/0048797 A1 | 3/2006 | Jung et al. |
| 2006/0066448 A1 | 3/2006 | Berisford et al. |
| 2006/0074405 A1 | 4/2006 | Malackowski et al. |
| 2006/0096046 A1 | 5/2006 | Hilscher et al. |

| | | | | | | |
|---|---|---|---|---|---|---|
| 2006/0145871 | A1 | 7/2006 | Donati et al. | GB | 2376758 | 12/2002 |
| 2006/0159533 | A1 | 7/2006 | Zeiler et al. | JP | 1989083268 | 3/1989 |
| 2007/0001005 | A1 | 1/2007 | White et al. | JP | 04-087127 | 3/1992 |
| 2007/0234493 | A1 | 10/2007 | Hilscher et al. | JP | 04-269906 | 9/1992 |
| 2008/0020351 | A1 | 1/2008 | Hilscher et al. | JP | 05-269024 | 10/1993 |
| 2008/0022470 | A1 | 1/2008 | Hilscher et al. | JP | 08-000358 | 1/1996 |
| 2008/0022501 | A1 | 1/2008 | Hilscher et al. | JP | 08-117030 | 5/1996 |
| 2008/0022503 | A1 | 1/2008 | Hilscher et al. | JP | 1996187125 | 7/1996 |
| 2008/0028549 | A1 | 2/2008 | Hilscher et al. | JP | 08-275961 | 10/1996 |
| 2008/0032265 | A1 | 2/2008 | Hilscher et al. | JP | 1998005041 | 1/1998 |
| 2008/0034515 | A1 | 2/2008 | Hilscher et al. | JP | 1998127346 | 5/1998 |
| 2010/0027582 | A1* | 2/2010 | Lane et al. .................. 374/142 | JP | 28-62873 | 3/1999 |
| | | | | JP | 199113638 | 4/1999 |

FOREIGN PATENT DOCUMENTS

| | | | | | |
|---|---|---|---|---|---|
| | | | JP | 11-318951 | 11/1999 |
| CN | 2124686 | 12/1992 | JP | 2001-37788 | 2/2001 |
| CN | 2149877 | 12/1993 | JP | 1998137040 | 5/2008 |
| CN | 2332378 | 8/1999 | SU | 749380 | 7/1980 |
| DE | 2413524 | 10/1975 | SU | 1542539 | 2/1990 |
| DE | 2826008 C2 | 6/1983 | SU | 1674789 | 9/1991 |
| DE | 3708801 A1 | 9/1988 | WO | WO 91/06258 | 5/1991 |
| DE | 4036373 C2 | 11/1990 | WO | WO 95/33419 | 12/1995 |
| DE | 3936714 | 5/1991 | WO | WO 97/24079 | 10/1997 |
| DE | 3937852 | 5/1991 | WO | WO 98/24527 | 6/1998 |
| DE | 4012413 | 10/1991 | WO | WO 98/55274 | 10/1998 |
| DE | 4036479 | 5/1992 | WO | WO 99/20202 | 4/1999 |
| DE | 3880015 | 9/1993 | WO | WO 99/53562 | 10/1999 |
| DE | 4422086 C1 | 6/1994 | WO | WO 00/39768 | 7/2000 |
| DE | 4305013 | 8/1994 | WO | WO 00/42584 | 7/2000 |
| DE | 19506129 | 2/1995 | WO | WO 00/47128 | 8/2000 |
| DE | 19518935 | 5/1995 | WO | WO 00/74591 | 12/2000 |
| DE | 29608164 | 5/1996 | WO | WO 01/08591 | 2/2001 |
| DE | 19627752 A1 | 7/1996 | WO | WO 01/32052 | 5/2001 |
| DE | 195 06 129 | 8/1996 | WO | WO 01/47392 | 7/2001 |
| DE | 19628574 | 3/1997 | WO | WO 01/91603 | 12/2001 |
| DE | 19545324 | 6/1997 | WO | WO 02/93881 | 1/2002 |
| DE | 29608167 | 9/1997 | WO | WO 02/083257 | 10/2002 |
| DE | 29709865 U1 | 10/1997 | WO | WO 02/098315 | 12/2002 |
| DE | 29915858 U1 | 9/1999 | WO | WO 03/054771 | 7/2003 |
| DE | 299 15 858 | 2/2000 | | | |
| DE | 19832607 | 5/2000 | | | |
| DE | 19921677 | 11/2000 | | | |
| DE | 19923104 A1 | 11/2000 | | | |
| DE | 10001502 | 3/2001 | | | |
| DE | 100 26 513 | 5/2001 | | | |
| DE | 10026513 | 5/2001 | | | |
| DE | 19953651 | 10/2001 | | | |
| DE | 10135257 | 2/2002 | | | |
| DE | 10045353 | 3/2002 | | | |
| DE | 10045067 | 4/2002 | | | |
| DE | 10101163 | 7/2002 | | | |
| DE | 102 25 232 | 12/2002 | | | |
| DE | 4243219 A1 | 12/2002 | | | |
| DE | 201 19 745 | 5/2003 | | | |
| DE | 10153863 | 5/2003 | | | |
| DE | 10154946 | 5/2003 | | | |
| DE | 102 47 698 | 4/2004 | | | |
| EP | 024992 | 6/1984 | | | |
| EP | 046169 | 8/1984 | | | |
| EP | 0085795 | 3/1987 | | | |
| EP | 285915 | 12/1988 | | | |
| EP | 0300345 | 1/1989 | | | |
| EP | 0435329 | 7/1991 | | | |
| EP | 440051 | 8/1991 | | | |
| EP | 391967 B1 | 8/1992 | | | |
| EP | 294548 B1 | 4/1993 | | | |
| EP | 624079 | 10/1993 | | | |
| EP | 0 634 151 | 3/1994 | | | |
| EP | 634151 | 3/1994 | | | |
| EP | 787469 A1 | 8/1997 | | | |
| EP | 848921 | 6/1998 | | | |
| EP | 1267664 | 6/2004 | | | |
| EP | 1379149 | 8/2004 | | | |
| EP | 1244373 | 7/2006 | | | |
| FR | 2832298 | 5/2003 | | | |
| GB | 1167444 | 10/1969 | | | |
| GB | 1246564 | 9/1974 | | | |
| GB | 2082713 | 3/1982 | | | |
| GB | 2117230 | 10/1983 | | | |
| GB | 2146893 | 5/1985 | | | |

OTHER PUBLICATIONS

Office Action from U.S. Appl. No. 10/872,075, dated May 15, 2007.
Office Action from U.S. Appl. No. 10/872,075, dated Jun. 4, 2009.
Office Action from U.S. Appl. No. 10/872,075, dated Aug. 1, 2006.
Office Action from U.S. Appl. No. 10/872,075, dated Oct. 31, 2007.
Office Action from U.S. Appl. No. 10/872,075, dated Dec. 10, 2008.
Office Action from U.S. Appl. No. 10/872,075, dated Dec. 27, 2006.
Office Action from U.S. Appl. No. 11/888,386, dated Dec. 3, 2009.
Office Action from U.S. Appl. No. 09/811,080, dated Feb. 3, 2004.
Office Action from U.S. Appl. No. 09/811,080, dated Oct. 1, 2004.
Office Action from U.S. Appl. No. 10/241,274, dated Jan. 14, 2005.
Office Action from U.S. Appl. No. 10/241,274, dated Sep. 1, 2006.
Office Action from U.S. Appl. No. 10/662,237, dated Feb. 18, 2005.
Office Action from U.S. Appl. No. 10/871,469, dated Jan. 9, 2007.
Office Action from U.S. Appl. No. 10/871,469, dated Jul. 25, 2006.
Office Action from U.S. Appl. No. 10/871,469, dated Aug. 24, 2005.
Office Action from U.S. Appl. No. 10/871,469, dated Dec. 27, 2007.
Office Action from U.S. Appl. No. 10/872,016, dated Feb. 7, 2006.
Office Action from U.S. Appl. No. 10/872,016, dated 02/23/20079.
Office Action from U.S. Appl. No. 10/872,016, dated Mar. 7, 2008.
Office Action from U.S. Appl. No. 10/872,016, dated Apr. 10, 2009.
Office Action from U.S. Appl. No. 10/872,016, dated Jun. 24, 2005.
Office Action from U.S. Appl. No. 10/872,016, dated Jul. 10, 2006.
Office Action from U.S. Appl. No. 10/872,016, dated Sep. 20, 2006.
Office Action from U.S. Appl. No. 10/872,016, dated Nov. 9, 2009.
Office Action from U.S. Appl. No. 11/257,603, dated Jan. 18, 2007.
Office Action from U.S. Appl. No. 11/257,603, dated Mar. 21, 2008.
Office Action from U.S. Appl. No. 11/257,603, dated May 15, 2007.
Office Action from U.S. Appl. No. 11/257,603, dated Aug. 30, 2007.
Office Action from U.S. Appl. No. 11/257,603, dated Sep. 20, 2006.
Office Action from U.S. Appl. No. 11/257,603, dated Nov. 25, 2008.
Office Action from U.S. Appl. No. 11/763,338, dated Mar. 24, 2009.
Office Action from U.S. Appl. No. 11/763,338, dated Jul. 10, 2008.
Office Action from U.S. Appl. No. 11/763,338, dated Dec. 4, 2008.
Office Action from U.S. Appl. No. 11/888,212, dated Mar. 17, 2009.
Office Action from U.S. Appl. No. 11/888,212, dated Mar. 21, 2008.

Office Action from U.S. Appl. No. 11/888,250, dated Jun. 30, 2008.
Office Action from U.S. Appl. No. 11/888,251, dated Mar. 17, 2009.
Office Action from U.S. Appl. No. 11/888,251, dated Mar. 21, 2008.
Office Action from U.S. Appl. No. 11/888,386, dated Mar. 3, 2009.
Office Action from U.S. Appl. No. 11/890,083, dated Mar. 16, 2009.
PCT Search Report for PCT/EP 01/02844, dated Aug. 8, 2001.
PCT Search Report for PCT/EP 01/02862, dated Jul. 31, 2001.
PCT Search Report for PCT/EP 02/01724, dated Jul. 17, 2002 for U.S. Appl. No. 10/241,274.
Finkenzeller, Laus, "RFID-Handbuch, Grundlagen und praktische Anwendungen induktiver Funkanlagen, Transponder und kontaktloser Chipkarten" [Trans: "RFID Handbook. Fundamentals and Practical Applications to Inductive Radio Communications, Transponders and Contactless Chip Cards"], Carl Hanser Verlag Munchen, $2^{nd}$ Edtiion, Chapter 3, pp. 29-58 w/title page and Impressum. Contents pp. vii-xviii, and Appendices 15.2 "Standards" and 15.3 "Literature" on pp. 393-406, (2000).
Herzer, Gieselher, "Der grosse Lauschangriff auf Ladendiebe" [transl. "The great surveillance of shoplifters"] in Physikalische Blaetter [transl: Physics Letters] vol. 57, (2001), No. 5, pp. 43-48.

Package rear and bottom panels of Bausch & Lomb Interplak Model PB-4B, marked © 1990 (color copy, 1 sheet).
Color photographs of Bausch & Lomb "Interplak" Model PB-6 style Handpiece with waterproof electronic travel protection switch (believed circa 1992 on sale in the United States) (6 views).
Package rear and bottom panels of Bausch & Lomb Interplak Model Pb-6, marked © 1992 (color copy, 1 sheet).
Product use instructions to Bausch & Lomb Interplak travel-style "Voyager" model TK-2 marked © 1991 (6 photocopies sheets containing cover and pp. 1-10).
"RFID Made Easy" Handbook by EM Microelectronic-Marin SA, 2074 Mann, Switzerland, copr 2000 and dated Mar. 2001 Rev. C/350, pp. 1-33.
Use instructions to Braun D5 electric toothbrush Type 4726 on sale in US, circa 1991, including description of "Travel lock" switch.
Color photographs of Bausch & Lomb "Interplak" Model PB-4B style Handpiece with travel protection switch and Toothbrush attachment (handpiece stamped "1D IA", believed circa 1992 on sale in the United States) (2 sheets with 7 views).

* cited by examiner

REPLACEABLE ACCESSORY FOR A SMALL ELECTRICAL APPLIANCE AND METHOD OF MONITORING THE USAGE OF THE ACCESSORY

FIELD OF USE

This invention relates to accessories, in need of replacement from time to time, for small electrical appliances, such as brush attachments for electric toothbrushes or shaving components for electric shaving apparatus, as well as to a method of determining the usage or the end of the period of use (wear limit) of an accessory.

BACKGROUND

WO 03/054771 A1 discloses an electric toothbrush comprising a handpiece and a replaceable brush attachment. The brush attachment accommodates a memory in which information identifying the brush attachment is stored. Furthermore, the brush attachment houses a transponder that delivers the information stored in the memory upon receiving an interrogation signal from an interrogation station. The handpiece houses a microcontroller capable of computing the cumulative usage of the identified brush attachment and writing it into the memory of the brush attachment. The handpiece is also equipped with an indicator for indicating the need for replacement of a brush attachment.

DE 102 47 698 A1 discloses an electric toothbrush comprising a handpiece and a replaceable bristle head. The handpiece is provided with a display on which an end of use indication for the bristle head can be shown.

SUMMARY

One aspect of the present invention provides an accessory for a small electrical appliance that enables the usage of the accessory to be readily monitored. Another aspect provides a simple method of determining the remaining period of use of the accessory.

According to one aspect of the invention, an accessory has a data memory, a transponder and electronic circuitry that modifies a value stored in the data memory each time it receives a corresponding signal from the small electrical appliance. The value stored in the data memory is, for example, a counter reading that corresponds to the cumulative usage of the accessory. Given a predetermined maximum period of use of the accessory, it is also possible to determine and store the remaining period of use, the end of the period of use, or a relative period of use relative to the maximum period of use.

Such an accessory has the advantage that the usage or period of use data is stored in the accessory itself, that is, there is no need for the small electrical appliance to distinguish the respective data of various accessories. This advantage is of particular importance in connection with an electric toothbrush, the handpiece of which is used by several family members by attaching their respective personal brush attachments. Similarly a handpiece may be operated with different types of brush attachments, for example, a cleaning brush and a massaging brush.

A small electrical appliance cooperating with the accessory preferably has a transmitting and receiving device enabling an interrogation signal to be sent and a signal returned by the transponder of the accessory to be received. In this way the data stored, for example, in the data memory of the accessory can be modified, read out and/or indicated on an indicator device. Data transmission between the small electrical appliance and the accessory can take place by high-frequency signals, for example, which preferably are transmitted inductively. In cases where an accessory has no power supply of its own, the transponder and the electronic circuitry are operated with a supply voltage obtained from the high-frequency field generated by the small electrical appliance.

A particularly simple construction of an exemplary accessory utilizes signal for modifying the stored value developing a supply voltage in the transponder each time the accessory reaches the transmission range of the small electrical appliance, e.g., when coupled thereto, or when the small electrical appliance with the coupled accessory is switched on. In this way a simple use counter is obtained which records accessory usage.

Another construction of an accessory modifies the stored value using signals which the small electrical appliance emits during operation, for example at one-second intervals. In this manner, a simple use counter is obtained which records the running time of the accessory to the second.

In another embodiment of an accessory, the electronic circuitry in the accessory increments the counter reading stored in the data memory by one step each time the small electrical appliance is switched on or upon receipt of a corresponding signal until a maximum value is reached. It is, however, also possible for the counter reading to be decremented from a predetermined value. The end of the useful life of the accessory can then be detected when the counter reading reaches ZERO. The respective counter reading is transmitted from the transponder to the small electrical appliance.

On each modification of the value stored in the data memory, the electronic circuitry reads the current value of the data memory, modifies the value and writes it back into the data memory. Preferably, a non-volatile memory, for example, an EEPROM, is used as data memory. Writing into a memory cell of an EEPROM takes several milliseconds and is conventionally preceded by setting all the bits in the memory cell to ZERO. If the power supply fails for example, a high-frequency field breaks down, the write operation is aborted. In consequence, the memory holds a meaningless value or the memory contents are lost.

Possible reasons for a failure of the high-frequency field are that the user turns the small electrical appliance off again or replaces the accessory, hence removing it from the small electrical appliance, or the primary or secondary cell of the small electrical appliance is depleted or supplies a voltage insufficient for building up the high-frequency field. The likelihood of the high-frequency field failing precisely during the short interval of time when data is written into the data memory may be low. However, when the accessory is used frequently as intended, the likelihood of losing the contents of the data memory increases.

An exemplary method for determining the usage or the end of the period of use of the accessory will now be described.

The counter reading of the use counter is stored in a non-volatile data memory to prevent data loss. Therefore, the data memory may include at least two memory cells, each holding a counter reading. A suitable data memory is an EEPROM, for example. In an unused accessory, each of the two memory cells initially contains a maxim value or ZERO, for example. In addition, each memory cell holds an identifier for the electronic circuitry to detect whether or not the value stored in the memory cell is correct or meaningful. For example, this identifier may be in the form of an additional bit, stored in the memory cell together with the respective counter reading. When a meaningful value is to be modified in one memory cell, it will not be overwritten by the modified value until it is confirmed that the other memory cell also holds a meaningful value.

DETAILED DESCRIPTION

Figure 1:
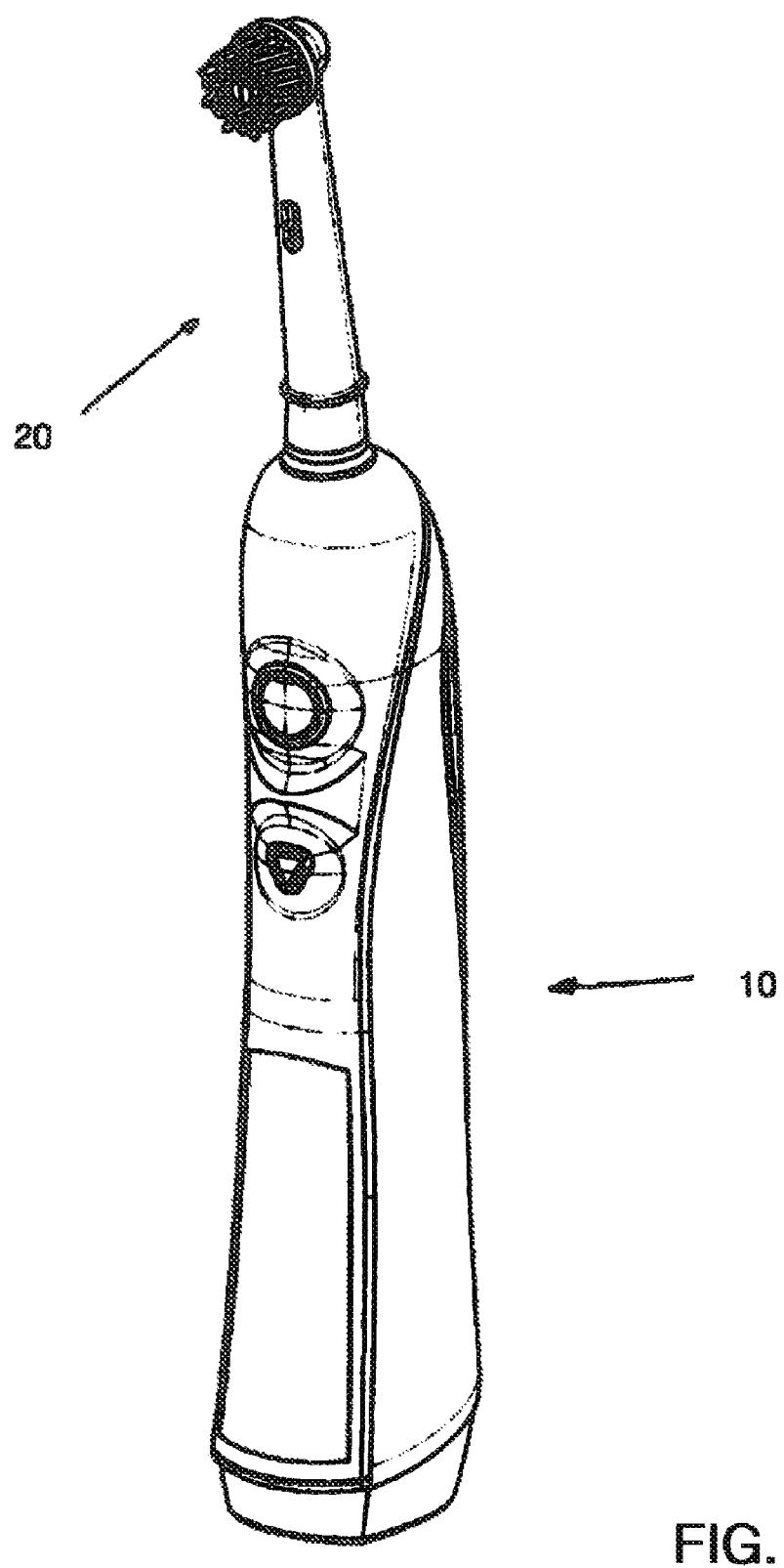
FIG. 1 is a perspective view of a small electrical appliance according to one embodiment.
Figure 2:
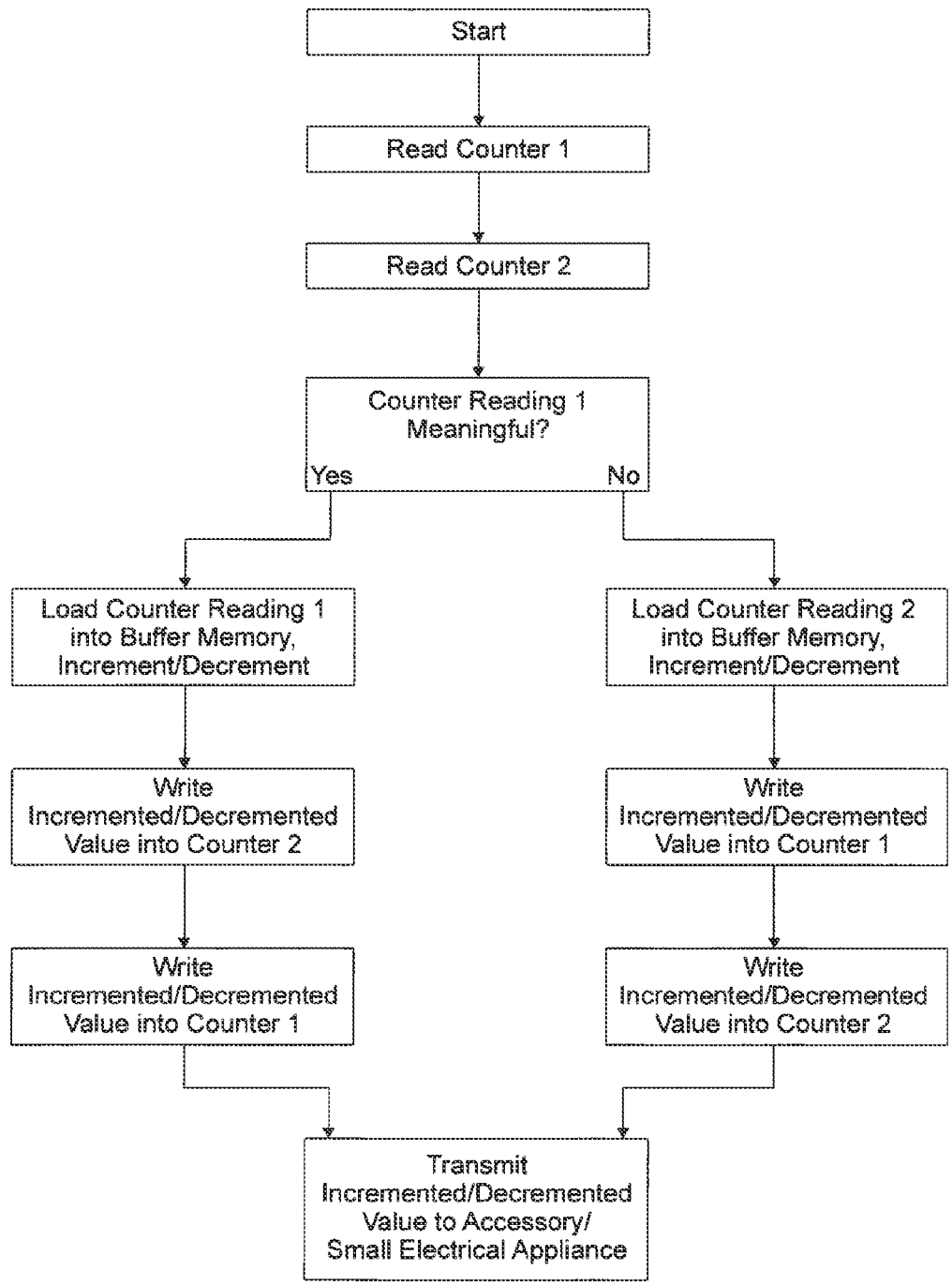
FIG. 2 illustrates a flow diagram for an exemplary method according to one embodiment.

FIG. 1 illustrates an exemplary small electrical appliance. In this embodiment, the small electrical appliance is an electric toothbrush 10. In one embodiment, the electric toothbrush 10 includes an accessory 20.

An exemplary method will be explained with reference to an embodiment illustrated in the accompanying FIG. 1 showing a flowchart.

After the transponder has emitted a corresponding signal, e.g., supply voltage, the electronic circuitry reads the counter reading from the first and second memory cell and establishes, by means of the identifier, whether the first memory cell holds a meaningful value. Provided the first memory cell holds a meaningful value, the counter reading of the first memory cell is loaded into a buffer memory and decremented by 1, for example. The decremented counter reading is stored in the second memory cell and then in the first memory cell. If the first memory cell contains no meaningful value, the counter reading of the second memory cell is loaded into the buffer memory and decremented by 1. The decremented counter reading is stored in the first memory cell and then in the second memory cell. Subsequently, the new counter reading is transmitted from the transponder to the small electrical appliance. This process sequence ensures that at the end both memory cells contain a meaningful value if one of the two memory cells contained a meaningful value at the beginning of the process. Thus, in the event of failure of the supply voltage of the accessory during the process, at least one of the two memory cells holds a meaningful value.

The small electrical appliance can indicate the received new counter reading on an indicator that indicates, for example, the projected remaining number of uses of the accessory. Alternatively, the indicating device may not be activated until the counter reading ZERO is transmitted, which signals that the accessory is spent and should be replaced.

The invention claimed is:

1. A method of monitoring usage of an accessory for a small electrical appliance, the method comprising:
    providing an accessory including a data memory and a transponder;
    coupling the accessory to a small appliance;
    modifying a value stored in the data memory each time the accessory receives a corresponding signal from the small electrical appliance wherein the data memory stores at least two values, each provided with an identifier, which correspond to the usage of the accessory;
    determining, by means of the identifier, whether one of the two stored values is meaningful; and
    in response to determining that one of the two stored values is meaningful, overwriting the meaningful stored value with a modified value when the accessory is used.

2. The method according to claim 1, further comprising transmitting the stored value from the transponder to the small electrical appliance.

3. The method according to claim 1, wherein providing an accessory comprises one of providing a toothbrush accessory and providing a shaving apparatus accessory, and wherein modifying the stored value is performed in response to usage of the accessory with the small appliance.

4. The method according to claim 1, wherein the stored value is modified to indicate at least one of a number of uses, a cumulative time of usage, and a projected end of usable life.

5. The method according to claim 1, wherein the signal received from the small appliance comprises a high frequency inducation signal.

6. The method according to claim 1, further comprising displaying an indicator that the accessory should be replaced, in response to the stored value reaching a predetermined value.

7. An accessory for a small electrical appliance comprising:
    an electronic circuit disposed within the accessory;
    a data memory coupled to the electronic circuit within the accessory;
    a transponder coupled to the electronic circuit and positioned within the accessory to receive signals from a small appliance with the accessory coupled to the small appliance;
    wherein the electronic circuit modifies a value stored in the data memory each time the transponder receives a particular signal from the small electrical appliance to which the accessory is coupled; and wherein the accessory does not have its own power supply and the signal for the modification of the stored value is a supply voltage building up in the transponder.

8. The accessory according to claim 7, wherein the electronic circuit modifies the value stored in the data memory each time the appliance is switched on with the accessory coupled to the appliance.

9. The accessory according to claim 7, wherein the value stored in the data memory is a counter that corresponds to accessory usage.

10. The accessory according to claim 9, wherein the electronic circuit increments or decrements the counter by one unit upon each receipt of the particular signal until the counter reaches one of a maximum or minimum value indicative of the need to replace the accessory.

11. The accessory according to claim 7, wherein the electronic circuit stores the modified value in the data memory.

12. The accessory according to claim 7, wherein the data memory is an EEPROM having at least two memory cells in which the counter can be separately stored.

13. The accessory of claim 7, wherein the small accessory is one of a brush attachment for use with an electric toothbrush and a shaving component for use with an electric shaving apparatus.

* * * * *